United States Patent [19]

Kurkov

[11] 4,044,050

[45] Aug. 23, 1977

[54] ISOMERIZATION OF PROPENYL ESTERS

[75] Inventor: Victor P. Kurkov, San Rafael, Calif.

[73] Assignee: Chevron Research Company, San Francisco, Calif.

[21] Appl. No.: 611,763

[22] Filed: Sept. 9, 1975

[51] Int. Cl.² .............................................. C07C 67/28
[52] U.S. Cl. ................................ 260/491; 260/410.6; 260/410.9 N
[58] Field of Search ............... 260/491, 410.6, 410.9 N

[56] References Cited

U.S. PATENT DOCUMENTS

| 3,755,451 | 8/1973 | Kurtz et al. | 260/491 |
| 3,830,833 | 8/1974 | Mabuchi et al. | 260/491 |

*Primary Examiner*—Vivian Garner
*Attorney, Agent, or Firm*—D. A. Newell; John Stoner, Jr.; W. Keith Turner

[57] ABSTRACT

Process for preparing propenyl ester isomers which comprises heating a mono or diacyloxy propene in the presence of a catalytic amount of a nitrile/palladium catalyst under conditions effective to convert the propenyl ester to its ester isomer.

5 Claims, No Drawings

ISOMERIZATION OF PROPENYL ESTERS

BACKGROUND OF THE INVENTION

This invention relates to a process for preparing propenyl esters of mono- and diacyloxy propenes utilizing a nitrile/palladium isomerization catalyst.

Mono- and diacyloxy propenes are employed in a variety of commercial processes. For example, diacyloxy propenes can be hydrolyzed and reduced to prepare saturated diols which are in turn useful in the synthesis of polyesters. However, for many commercial processes, such as the synthesis of polyesters, it is desirable to employ acyloxy propenes having terminal reactive groups. For example, the synthesis of polyesters employs the 1,3-diacyloxy propenes in preference to the 1,1-isomer. Accordingly, there is a need for a process for preparing propenyl esters or mono- and diacyloxy propenes having terminal acyloxy groups. Toward this aim, it has been found that nitrile/palladium complexes are highly effective propenyl ester isomeriation catalysts.

The use of select palladium catalysts to initiate isomerization reactions is described in the prior art. For example, palladium acetate has been suggested to catalyze the isomerization of butenyl acetate and propionate; see P.M. Henry, *Chem. Comm.* 1971, p. 328. However, the effectiveness of catalysts generally, and isomerization catalysts in particular, is often influenced by even minor atomical variations in the catalyst itself or the material to be isomerized. For example, it has been found that palladium acetate will not successfully catalyze the rearrangements of diacyloxy esters such as 3,4-diacetoxy-1-butene, whereas it has been found that nitrile/palladium complexes are extremely active.

Strong acids, such as sulfuric acid, have also been suggested as suitable isomerization catalysts; see Smith, et al., *J. Amer. Chem. Soc.* 73, 1951, p. 5282. However, the reported equilibrium conversion to rearranged isomer is relatively low, and the process requires either high reaction temperatures or long reaction times.

Thus, there is a continuing need to provide a process for preparing the isomers of mono and diacyloxy propenes.

SUMMARY OF THE INVENTION

It has now been found that propenyl esters of mono and diacyloxy propenes are isomerized when heated to a temperature of from about 25° to 150° C in the presence of a catalytic amount of a nitrile/palladium complex.

DETAILED DESCRIPTION OF THE INVENTION

The process of this invention comprises isomerizing a mono or diacyloxy propene in the presence of a catalytic amount of a nitrile/palladium complex. The isomerization reaction involved in this process proceeds according to the reaction scheme

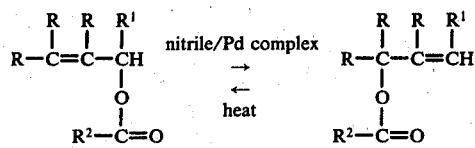

wherein each R is independently selected from the group consisting of hydrogen and lower alkyl; $R^1$ is selected from the group consisting of hydrogen, lower alkyl, $-O-C(O)R^2$, and $-CH_2-O-C(O)R^2$; and $R^2$ is lower alkyl. As used herein the term "lower alkyl" is intended to encompass straight- or branched-chain alkyl moieties containing from 1 to about 10 carbon atoms, preferably from 1 to about 5 carbon atoms. Thus, the present invention contemplates the reversible isomerization of mono- and diacyloxy propenes.

Monoacyloxy propenes preferred for use in the practice of this invention are otherwise known as alkenyl aliphatic carboxylates and are readily prepared by a variety of well-known reactions. For example, alkenyl carboxylates can be prepared by direct esterification of a carboxylic acid with an alkenol; or by the reaction of a carboxylic acid with carbonium ions from alkenols or alkenes. A thorough review of these and other carboxylate preparations can be found in Noller (ed.). *The Chemistry of Organic Compounds* 3rd, 1966, p. 183 et seq.

In accordance with the above formulas, monoacyloxy propenes (alkenyl carboxylates) preferred for use in the practice of this invention include compounds wherein substituents R and $R^1$ may be hydrogen or lower alkyl such as methyl, ethyl, propyl, butyl, isopropyl, isobutyl, neopentyl, hexyl, decyl, and the like; and substituent $R^2$ is lower alkyl such as methyl, ethyl, propyl, butyl, hexyl, isobutyl and the like. Alkenyl acetates, those compounds wherein substituent $R^2$ is methyl, are especially preferred monoacyl propenes. Illustrative alkenyl acetates include, for example:

propenyl acetate;
butenyl acetate;
2-methylbutenyl acetate;
2-methylpropenyl acetate;
pentenyl acetate;
3-methylpentenyl acetate;
decenyl acetate; and the like.

The diacyloxy propenes, represented above, which are preferred for use in the practice of this invention are otherwise known as alkenyl dicarboxylates and are readily prepared by a variety of well-known reactions. For example, alkenyl dicarboxylates can be prepared by acylation of the corresponding alkenediol. This reaction is thoroughly described by W. E. Bissinger, et al., *J. Amer. Chem. Soc.* 69, 1947, p. 2955. Alternatively, alkenyl dicarboxylates can be prepared by acylation of an alkenediol with a carboxylic acid anhydride.

In accordance with the above formulas, diacyloxy propenes (alkenyl dicarboxylates) preferred for use in the practice of this invention include compounds wherein substituents R may be hydrogen or lower alkyl such as methyl, ethyl, propyl, butyl, isobutyl, hexyl, neopentyl, decyl and the like; substituent $R^1$ is acyloxy or acyloxy methylene; and substituent $R^2$ is lower alkyl such as methyl, ethyl, hexyl, octyl and the like. Alkenyl diacetates, those compounds wherein $R^2$ is methyl, are especially preferred diacyloxy propenes. Illustrative alkenyl diacetates include, for example:

propenyl-1,2-diacetate;
butenyl-1,2-diacetate;
hexenyl-1,2-diacetate;
propenyl-1,4-diacetate;
butenyl-1,4-diacetate;
propenyl-1,1-diacetate;
butenyl-1,1-diacetate;
propenyl-1,3-diacetate;
butenyl-1,3-diacetate and the like.

Especially preferred diacyloxy propenes suitable for use in the practice of the present process include propenyl 1,1-diacetate and butenyl 1,2-diacetate.

It has been found that nitrile/palladium-based complexes effectively catalyze the isomerization of the mono and diacyloxy propenes described above. Nitrile/palladium complexes are well-known compounds. For example, Hartley, *Organometallic Chem.* 46, 1973, p. 119 describes illustrative nitrile/palladium halide complexes which are suitable for use herein. In general, suitable catalytic nitrile/palladium complexes are characterized by a nitrile, i.e., organic cyanide, ligand and a palladium moiety.

Suitable nitrile ligands, either mono or dinitrile, may contain aliphatic or aromatic substituents. Illustrative aliphatic nitrile ligands include, for example, nitriles of the formula $R^4C\equiv N$ wherein $R^4$ is straight- or branched-chain substituted or unsubstituted alkyl or alkenyl containing from 1 to about 7 carbon atoms. Illustrative polymeric nitrile ligands include, for example, nitriles of the formula:

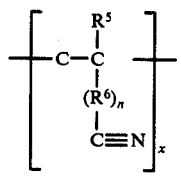

wherein $R^5$ is hydrogen or methyl; $R^6$ is phenyl or benzyl; $n$ is 0 or 1; and X is the degree of polymerization. Representative aliphatic nitrile ligands include, for example, acetonitrile, acrylonitrile, propiononitrile, lauronitrile, pentadecane-nitrile, and butyronitrile. Aliphatic polymeric nitrile ligands include, for example, polyacrylonitrile, polymethylacrylonitrile, and p-cyanomethylpolystyrene.

Illustrative aromatic nitrile ligands include mono- and polynuclear aromatic nitriles. Representative mononuclear nitrile ligands suitable for use herein include, for example benzonitrile, p-methylbenzonitrile, o-terephthalonitrile and m-chlorobenzonitrile. Illustrative polynuclear aromatic nitrile ligands include, for example, naphtalene cyanide, anthracene cyanide, and the like.

Preferred nitrile/palladium-based catalysts used in the practice of the present process are generally described by the formula

wherein L is the nitrile ligand; X is halogen complexed to the palladium; $n$ is 2; $m$ is 1 to 2; and $m + n$ is 3 to 4. It is apparent that $m + n$ represents the coordination number of palladium, i.e., two-, three-, or four-coordinate and $m$ represents the valence or oxidation state of the palladium. In accordance with this formula, suitable halogen ligands complexed to palladium include, for example, chloride, bromide, and iodide.

The most preferred catalyst is bis-benzonitrile/palladium chloride having the formula:

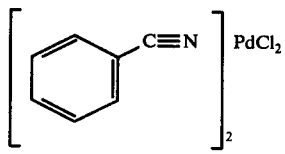

The amount of catalyst present in the system is not critical and can vary over a wide range. However, in general, the rate of reaction will vary in proportion to the quantity of catalyst employed. Under normal conditions, the nitrile palladium halide can be used in amounts ranging from about 0.1 to about 10.0% by weight based of the mono or diacyloxy precursor. It may be desirable to initiate the isomerization using lower concentrations of catalyst and, thereafter, introduce additional catalyst to the reaction mixture. This procedure is especially useful when performing the reaction at the lower reaction temperatures.

The isomerization reaction is carried out at a temperature in the range from about 25° to about 150° C, preferably from about 50° to 100° C. While the rate of reaction is influenced by, for example, the choice and quantity of catalyst employed, the reaction temperature, and the substrate isomerized, in general, complete reaction times will vary from 15 to 90 minutes.

The process of this invention yields a mixture of isomers which may be separated by conventional separation techniques such as distillation. The unisomerized starting material may then be recycled, and the desired ester may be recovered.

EXAMPLES

The following examples illustrate the practice of this invention.

EXAMPLE 1

Isomerization of cis-1,4-diacetoxy-2-butene 100.1 g (0.580 mol) of cis-1,4-diacetoxy-2-butene (prepared by acetylation of 2-butene-1,4-diol) and 2.5 g (5.6 mmols) of bis-benzonitrile palladium chloride (prepared by the procedure described in Hartley, supra) were placed in a 250-ml flask provided with a reflux condenser. The assembly was immersed in an oil bath set at 100° C. After 30 minutes, gas chromatographic analysis showed the following distributions of products (identified by comparison with authentic samples):

|  | Mol % |
|---|---|
| 3,4-diacetoxy-1-butene | 41.5 |
| 1,4-diacetoxy-1-butene | 3.6 |
| cis-1,4-diacetoxy-2-butene | 9.2 |
| trans-1,4-diacetoxy-2-butene | 45.7 |

The product composition did not change with time, indicating an equilibrium distribution.

The products were separated from the catalyst by flash distillation b.p. 40°-70° C at 0.07 mm Hg. The final separation was accomplished by vacuum distillation through a 12inch packed column. 44 g of 3,4diacetoxy-1-butene, b.p. 56°-62° C at 10.4 mm Hg and 31 g of 1,4-diacetoxy-2-butene, b.p. 74°-77° C at 10.4 mm Hg were recovered.

An equivalent amount of 3,4-diacetoxy-1-butene, 3,3-diacetoxy-1-propene and 1,3-diacetoxy-1-propene, respectively, are substituted for 1,4-diacetoxy-2-butene in the above procedure and isomerized in a like fashion.

EXAMPLES 2-7

Isomerization using various palladium-based catalysts

Using the procedure of Example 1, on a 1/50th scale and without distillation, 1,4-diacetoxy-2-butene was isomerized to prepare an equilibrium mixture of isomers using a variety of palladium catalysts. The conditions of isomerization and product distributions are tabulated in Table I.

The catalyst was filtered off. 2 g of triphenylphosphine was added to the filtrate and the filtrate distilled through a 22 inch packed column at 1 mm Hg.

TABLE I

PRODUCTS FROM ISOMERIZATION OF CIS-1,4-DIACETOXY-2-BUTENE[1] at 100° C

| Example | Catalyst | Time hrs. | Cis-1,4-diace-toxy-2-butene | Trans-1,4-diace-toxy-2-butene | 3,4-diace-toxy-1-butene | 1,4-diace-toxy-1-butene |
|---|---|---|---|---|---|---|
| 2 | $(\phi CN)_2OdCl_2$[2] | ½ | 9.2 | 45.7 | 41.5 | 3.6 |
| 3 | | 2 | 8.9 | 52.7 | 34.3 | 4.0 |
| | $(\phi CN)_2PdCl_2$ | 4 | 9.5 | 52.1 | 33.8 | 4.6 |
| | | 6 | 9.1 | 52.7 | 33.8 | 4.4 |
| 4 | $PdCl_2$[3] | 18 | 19 | 51 | 30 | — |
| 5 | $(Py)_2PdCl_2$[3] | 4-½ | 95.1 | 3.4 | 1.5 | — |
| 6 | $(\phi_3P)_2PdCl_2$[3] | 18 | 95.1 | 3.4 | 1.5 | — |
| 7 | $Pd(OAc)_2$[3] | 18 | 96.1 | 3.9 | 0 | — |

[1]Heated under reflux conditions. Contained 1.3 mol% catalyst.
[2]Run 50 33 0 scale.
[3]Commercial materials.
$\phi$ = phenyl
Ac = acetate
Py = pyridine Table I illustrates the effect of various palladium-based catalysts on isomerization. Bis-benzonitrile/palladium chloride catalyzed the isomerization reaching equilibrium in 30 minutes, while palladium chloride required more than 18 hours. Bis-pyridine palladium chloride, bis-triphenylphosphine palladium chloride and palladium acetate were inactive.

EXAMPLE 8

Isomerization of allylidine diacetate

This example illustrates the isomerization of allylidine diacetate, prepared by the procedure of C. W. Smith et al., *J. Amer. Chem. Soc.* 73, 1951, p. 5282, using a polyacrylonitrile/palladium chloride catalyst. The catalyst was prepared according to the following procedure: 5 grams of polyacrylonitrile (Polysciences) and 0.5 grams of bis-benzonitrile palladium chloride were stirred in 50 milliliters of benzene at room temperature, overnight. The resin was filtered off, washed with ennzene and dried in vacuo at 60° C.

Polyacrylonitrile palladium chloride, although slower than the monomeric nitrile complex, offers the advantage of being easily separated from the products by filtration, because it is substantially insoluble in the reaction medium.

153.9 g (0.97 mol) of allylidine diacetate and 10 g of polyacrylonitrile-$PdCl_2$ were stirred in a 250-ml, round-bottom flask under a reflux condenser in an oil bath at 100° C. Chromatographic analyis indicated the following product distribution as a function of time:

| Products | Time 30' | 60' | 420' |
|---|---|---|---|
| Allylidine diacetate | 71.4% | 68.5% | 62.9% |
| cis-1,3-diacetoxy-1-propene | 4.0% | 5.9% | 12.1% |
| trans-1,3-diacetoxy-1-propene | 24.6% | 27.7% | 25.0% |

During distillation the following cuts were collected and analyzed:

| Cut | b.p., ° C | Wt. g | 1,1— | 1,3— |
|---|---|---|---|---|
| 1 | 41–45 | 15 | 93.4 | 1.0 |
| 2 | 45–47 | 61 | 88.1 | 10.1 |
| 3 | 47–61 | 16 | 48.1 | 48.6 |
| 4 | 61 | 13 | 14.1 | 85.9 |
| Bottoms | | 6 | 28.6 | 71.2 |

EXAMPLE 9

Effect of time and temperature

The effect of various reaction temperatures and times on the isomerization product distribution were analyzed using three 25-ml, two-necked, round-bottom flasks provided with a reflux condensor, serum cap and a magnetic stirrer. Each flask was charged with 5.1 grams of allylidine diacetate, 2.2 grams of toluene and 0.12 grams of bis-benzonitrile palladium chloride.

Each assembly was immersed in oil baths at 100° C, 50° C or 21.5° C. Samples at each temperature were withdrawn for gas chromatographic analysis. The results are shown in Table II.

TABLE II

| | | Effects of Temperature and Time Products, Mol% | | |
|---|---|---|---|---|
| Temperature, ° C | Time, Min. | 1,1-diacetoxy-2-propene | trans 1,3-diacetoxy-2-propene | cis 1,3-diacetoxy-2-propene |
| 100° C | 15 | 47.0 | 18.5 | 22.3 |
| | 30 | 58.1 | 18.4 | 20.7 |
| | 45 | 53.2 | 18.9 | 22.5 |
| 50° C | 10 | 66.4 | 12.5 | 18.2 |
| | 20 | 64.8 | 14.3 | 17.9 |
| 21.5° C | 30 | 72.2 | 8.0 | 17.9 |
| | 90 | 68.7 | 12.2 | 17.1 |

While the character of this invention has been described in detail with numerous examples, this has been done by way of illustration only and without limitation of the invention. It will be apparent to those skilled in the art that modifications and variations of the illustrative examples may be made in the practice of the invention within the scope of the following claims.

What is claimed is:

1. A process for preparing propenyl ester isomers which comprises heating a diacyloxy propene selected from the group consisting of compounds of the formulas

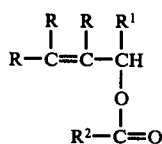

and

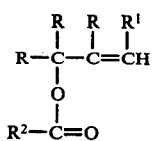

wherein each R is independently selected from the group consisting of hydrogen and lower alkyl; $R^1$ is selected from the group consisting of, $-O-C(O)R^2$, and $-CH_2-O-C(O)R^2$; and $R^2$ is lower alkyl at a temperature of from about 25° to about 150° C in the presence of a catalytic amount of a nitrile/palladium complex of the formula $$(L)_m Pd(X)_n$$

wherein L is a nitrile ligand; X is halogen complexed to palladium; $n$ is 2; $m$ is 1 to 2; and $m + n$ is 3 to 4.

2. A process according to claim wherein said propene is a diacetoxy propene.

3. A process according to claim 2 wherein said propene is a diacetoxy propene selected from the group consisting of propenyl-1,1-diacetate and butenyl-1,2-diacetate.

4. The process of claim 1, wherein said nitrile/palladium complex is bis-benzonitrile/palladium chloride.

5. The process of claim 1, wherein said catalyst is present in an amount ranging from about 0.1 to 10%, by weight relative to said diacyloxy propene.

* * * * *